US006110078A

United States Patent [19]

Dyer

[11] Patent Number: 6,110,078

[45] Date of Patent: Aug. 29, 2000

[54] PASSIVE STRETCHING DEVICE FOR PLANTAR FASCIA

[76] Inventor: Allen Miles Dyer, 3137 Glencliff Rd., Nashville, Tenn. 37211

[21] Appl. No.: 09/283,138

[22] Filed: Mar. 31, 1999

Related U.S. Application Data

[60] Provisional application No. 60/092,479, Jul. 10, 1998, and provisional application No. 60/103,204, Oct. 6, 1998.

[51] Int. Cl.[7] .......................... A63B 23/08; A63B 21/02; A61F 5/00

[52] U.S. Cl. .......................... 482/79; 482/121; 482/907; 602/27; 602/28

[58] Field of Search .......................... 602/5, 15, 16, 602/27–29, 60–62; 128/881, 882; 482/79; 601/33, 34; 600/592

[56] References Cited

U.S. PATENT DOCUMENTS

| | | | |
|---|---|---|---|
| 2,536,454 | 1/1951 | McIntyre | 602/28 |
| 2,591,378 | 4/1952 | Scholl | 602/30 |
| 4,351,324 | 9/1982 | Bronkhorst | 602/27 |
| 4,474,176 | 10/1984 | Farris et al. | 601/64 X |
| 4,669,450 | 6/1987 | Lindberg | 601/33 |
| 4,693,470 | 9/1987 | Ogawa . | |
| 4,955,370 | 9/1990 | Pettine | 602/28 |
| 4,962,760 | 10/1990 | Jones | 602/27 |
| 5,144,943 | 9/1992 | Luttrell et al. | 601/34 |
| 5,358,469 | 10/1994 | Patchel et al. . | |
| 5,368,281 | 11/1994 | Skyba . | |
| 5,399,155 | 3/1995 | Strassberg et al. . | |
| 5,453,082 | 9/1995 | Lamont | 602/27 |
| 5,486,157 | 1/1996 | Dibendetto . | |
| 5,542,912 | 8/1996 | Hess | 602/27 |
| 5,569,173 | 10/1996 | Varn | 602/27 |
| 5,611,770 | 3/1997 | Tesch | 601/34 |
| 5,645,516 | 7/1997 | Foster . | |
| 5,665,059 | 9/1997 | Klearman et al. . | |
| 5,700,237 | 12/1997 | Hess | 602/27 |
| 5,776,090 | 7/1998 | Bergman et al. . | |
| 5,887,591 | 3/1999 | Powell et al. | 128/882 |

*Primary Examiner*—Mickey Yu
*Assistant Examiner*—Denise Pothier

[57] ABSTRACT

A device consisting primarily of two hinged plates with a variable tensioning mechanism. Applied to the foot and lower leg the device provides a progressive stretch for planter fascia, Achilles tendon and gastrocnemius muscle. Enhancements, comprised of an adjustable toe support, adjustable arch support and foot strap enable maximization of stretch for various foot types and conditions. A method of setting tension levels allows for application of protocol and, in conjunction with the use of a system to measure angular displacement of the plates, provides a method of evaluating flexibility and flexibility gains of the plantar fascia/Achilles tendon system.

17 Claims, 10 Drawing Sheets

PASSIVE STRETCHING DEVICE FOR PLANTAR FASCIA

CROSS-REFERENCE TO RELATED APPLICATIONS

This application is related to provisional applications Ser. Nos. 60/092,479, filed Jul. 10, 1998 and 60/103,204, filed Oct. 6, 1998, on a developmental continuum of the device described therein.

BACKGROUND

This invention relates to the field of rehabilitation devices and stretching devices in particular.

The plantar fascia is a sinuous band that attaches between the calcaneous bone of the heel and the metatarsals located in the front part of the human foot. Traumatic or, most often, chronic overstressing of this band leads to inflammation, as well as to tearing and shortening of the tissue through scarring. The resulting condition, which is commonly referred to as "plantar fasciitis", presents with mild to severe heel pain which, if left untreated, can interfere with walking and daily living activities, as well as athletic activity. This condition is diagnosed in both the athletic and sedentary population, and is especially common in the obese and in people who exercise on hard surfaces.

Non-surgical treatment of this condition often involves both anti-inflammatory agents (both systemic and topical) as well as lengthening the plantar fascia through a stretching routine designed to relieve the tension at the point of attachment to the heel.

Unfortunately, traditional active stretching techniques necessary to achieve an effective lengthening of the planter fascia, require more involvement and discipline than the average patient is likely to manifest. A device that can passively, comfortably and conveniently hold the foot in a developmental stretch while the patient sits or reclines would significantly increase compliance in a rehabilitation program and would perhaps alleviate the need for surgical intervention. Compliancy issues such as simplicity in applying and adjusting the device should be considered. In order to facilitate this developmental stretch, this device should be progressive, allowing for a variable amount of stretching, from mild to extreme, based on the patient's needs and foot structure. The ease of adjusting the intensity of the stretch will have relevancy as a compliancy issue. This device should also address the systemic nature of the plantar fascia, i.e., its interaction with the Achilles tendon and gastrocnemius muscle. It can be inferred that such a device would also be useful in addressing shortened length issues of the Achilles tendon and gastrocnemius muscle. Further, this device should be able to provide and customize the various components of a complete and effective stretch, i.e., dorsiflexion, toe bend, arch compression and gastrocnemius stretch. In addition, a device that is amenable to setting protocol and evaluating flexibility and flexibility gains would clearly have an advantage.

For such a common injury, there have been few attempts at providing a therapeutic device that could improve outcome, particularly by a developmental lengthening. There is a paucity of devices that will provide for all components of an effective stretch, i.e. dorsiflexion, toe bend, arch compression and gastrocnemius tensioning. Progressivity issues, compliance issues, quantification for protocol and evaluation issues have not been well developed in prior art.

Various orthoses, such as U.S. Pat. No. 5,665,059 to Klearman et al. and U.S. Pat. No. 5,486,157 to Dibendetto, while addressing an issue of dorsiflexion, can not provide either appropriate toe bend or arch compression. Such devices are not imbued with significant progressivity features nor are they amenable to quantifying the nature of a stretch for use in protocol. In fairness, this does not relate to the intended application of those types of devices.

U.S. Pat. No. 5,399,155 to Strassberg et al., described as a sock, and U.S. Pat. No. 5,776,090 to Bergmann et al., described as a splint, are designed merely to prevent contracture during long periods of inactivity and do not well address the various issues of developmental lengthening.

U.S. Pat. No. 5,358,469 to Patchel et al, described as a splint, while capable of addressing the issue of dorsiflexion and being a versatile device, is unable to provide all components of a stretch for plantar fascia. Again, in fairness, developmental lengthening of the plantar fascia is not the intended application for this device.

Exercisers such as U.S. Pat. No. 4,693,470 to Ogawa and U.S. Pat. No. 5,645,516 to Foster, while relating to dorsiflexion, are not by nature passive devices and also do not well address the various issues of developmental lengthening for planter fascia.

SUMMARY

The object of this device is to provide a corrective therapy, by developing length, for plantar fascia, Achilles tendon and gastrocnemius muscle as affected by shortened length issues, such as that of plantar fasciitis and to provide a maintenance regimen for those affected parts when length has been reestablished. Rather than simply limiting contraction, this device strives for a true and significant lengthening of those parts. Fundamental to this corrective action is a sustained stretch, for such duration, frequency and tension that overtime, these structures may develop a true increase in length. For example, protocol may indicate an intermittent stretching session of 10 to 30 minutes twice a day for a period of four weeks to six months. A similar stretching session before activity, producing a transitory lengthening, will minimize further trauma to those who are in the healing process. Particularly, for plantar fascia, development of a complete stretch would include dorsiflexion, toe bend and, for some foot types, particularly those with flat arch, a measure of arch compression. Gastrocnemius stretching may also benefit this process.

A variable dorsiflexion is achieved when the sole of the foot is placed against a foot plate and the calf of the lower leg against a leg plate, with the two plates forming a hinged joint at the heel, and the open ends of the respective plates are pulled together, as in the preferred embodiment, with a cinching device coupled to a steel tension spring, that together comprise a variable tensioning mechanism. The tensioning element, a spring, grants a dynamic property, allowing the foot to move and adjust while maintaining tension in the stretch. This spring tensioning element provides a wide variation in tensioning force, while the cinching mechanism allows a fine increment in adjustment. They are employed in such a way that variation is uncomplicated, i.e., adjustments are quick and easy and do not interrupt the application. The amount of tension in which dorsiflexion is held is determined by the tensile lengthening of the spring, which is adjusted with the cinching mechanism. Discrete levels of dorsiflexed tension can be defined by the length of the steel spring. As the spring is lengthened, tension is increased relative to its spring constant value. As incremental marks along the length of the spring align with the end of a gauge stick, tension levels can be set. In such a manner, a protocol may be defined that could maximize the benefit of the device for the user and minimize the risk of over-stretching in initial therapy sessions, allowing any increment of tension from very mild to very stiff.

To enhance the stretch of the planter fascia, two optional elements are supplied. The first of these is a toe support that will cause the toes to the bend backwards substantially, towards the top of the foot, further tensing the plantar fascia while the foot is already in dorsiflexion. The second of these optional attachments is an arch support, adjustable in height by inserting a variable thickness of foam material into its center. This particular enhancement becomes more significant to those who have flatter arches and do not feel a complete stretch with only dorsiflexion and toe bend.

In addition to being amenable to protocol, this device also allows for a determination of flexibility and flexibility gains. This is achieved through an indirect measurement of the angle between the foot plate and leg plate. By triangulation, a measuring rod, with one end set in a locating depression on the leg plate, will align on the other end with a scale, imprinted on the foot plate, that corresponds to the angle between the two plates. Such measurement, taken under a defined and constant amount of tension, becomes the basis for evaluation of flexibility and gains thereof. This method of measurement, coupled with the ability to set discrete tension levels, will also lend itself to an evaluation of the effectiveness of the various components of the stretch. This is because a portion of the total stretch tension is transferred from the Achilles tendon to the plantar fascia with the use of the toe support and arch support and, under a defined tension setting, a consequential variation in angular displacement will be noted. A heel placement guide on the foot plate will eliminate measurement errors due to inconsistent foot positioning, as well as preventing irritation to the back of the heel and Achilles tendon area by spacing them from the leg plate.

The foot is secured within the device by a cushioned foot strap. As convenience engenders compliancy, many users will find the foot strap unnecessary in some applications, as their foot may be secure within the device without its use. For those who require arch compression, the foot strap will be essential.

In an additional application of the device, a stretch can also be applied to the gastrocnemius muscle. This is achieved by simply straightening the leg at the knee, with the foot held in dorsiflexed tension by the device, and secured by the foot strap. In this manner, the device is useful in addressing length issues of the gastrocnemius as well as in addressing the systemic nature of the planter fascia, Achilles tendon and gastrocnemius muscle.

The features of this device that encourage compliancy are significant. Once applied to the foot and lower leg, this device requires no active participation of the user in the stretching process, i.e. it is passive in nature. Tension levels are quickly and easily changed while the foot is within the device. Once the device is set up for the users' foot, application is quick and simple, requiring, at most, the fastening of one strap. Tension levels are easily set by pulling the loose rope end of the cinching device. Padding is added to make the device more comfortable and to further and stabilize the foot within the device.

Simple construction and the use of commonly available and inexpensive components would lend to the manufacture of a product that is very affordable for the user.

DETAILED DESCRIPTION

Figure 1:
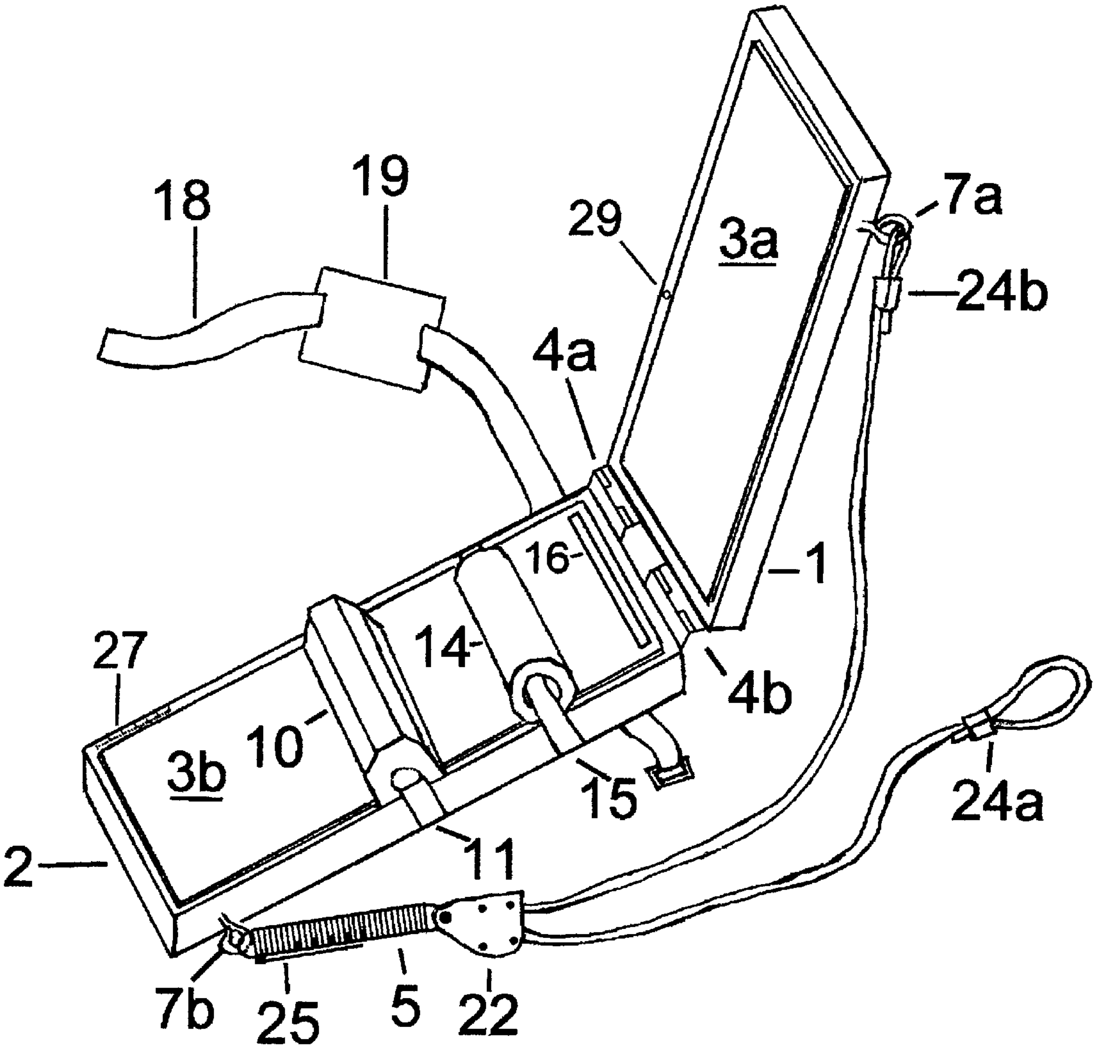
FIG. 1 shows and unobstructed view of the device with toe and arch supports attached.

As shown in FIG. 1, a leg plate (1) and a foot plate (2) are joined by a hinge (4A) and a hinge (4B). The plates are typically composed of wooden board, but could be composed of other appropriate rigid material, such as a polymer. Dimensions of the plates should be appropriate for the physical dimensions of the user. The device could be produced in a limited number of standard sizes adaptable to most users. The thickness of each plate is typically 314 inch to 1 inch. A width of 5 inches for each plate would accommodate a wide variety of feet. The length of the foot plate (2) would typically be 16 inches, but can vary as necessary. The length of the leg plate (1) should be such that its' end is 1 to 3 inches vertically below the knee joint. For most users, this value would range between 12 and 18 inches. The use of two hinges (4A and 4B) located at opposite extreme ends of the joint, rather than a single centrally located hinge, allow for maximum stability of the hinged joint. The hinges are appropriately positioned and secured to the ends of the plate with screws.

A pad (3A) and a pad (3B) are attached respectively to the leg plate (1) and the foot plate (2) with adhesive and serve to cushion and stabilize the calf of the leg and the foot within the device. The pads are constructed from an appropriate high density foam material and shaped to the dimensions of the leg of plate (1) and the foot plate (2), leaving a ½ inch margin on all edges. Thickness of the material would typically range from ¼ inch to ½ inch and would instigate positioning of hinges (4A and 4B) such that the plates can close upon themselves neatly. A heel placement guide (16) is comprised of a 3 inch piece of contrastingly colored tape and is located 1½ inches from the hinged end of the foot plate (2).

A dynamic tensioning mechanism consists of a spring (5) and a cinching mechanism (22). The spring (5) is of appropriate length and spring constant such that suitable range of tensions can be adjusted by the user. The spring (5) is attached on one end to the foot plate (2) by an eye screw **(7*b*) and on the other end is attached to the cinching mechanism (22). Upon attachment, the hook ends of the spring (5) are forcibly closed such that the spring may not be removed. Typically, the cinching mechanism (22) would be comprised of components of a previously patented cinching device, such as Rope Ratchet (U.S. Pat. No. 5,368, 281), including rope and ratchet mechanism. The rope fixed end of the cinching mechanism (22) is attached to the leg plate (1) by a eye screw (7*a*) and secured by a rope ferrule (24*b*). A rope ferrule (24A) serves to form a pull loop at the free end of the cinching mechanisms' (22)** rope.

Figure 3:
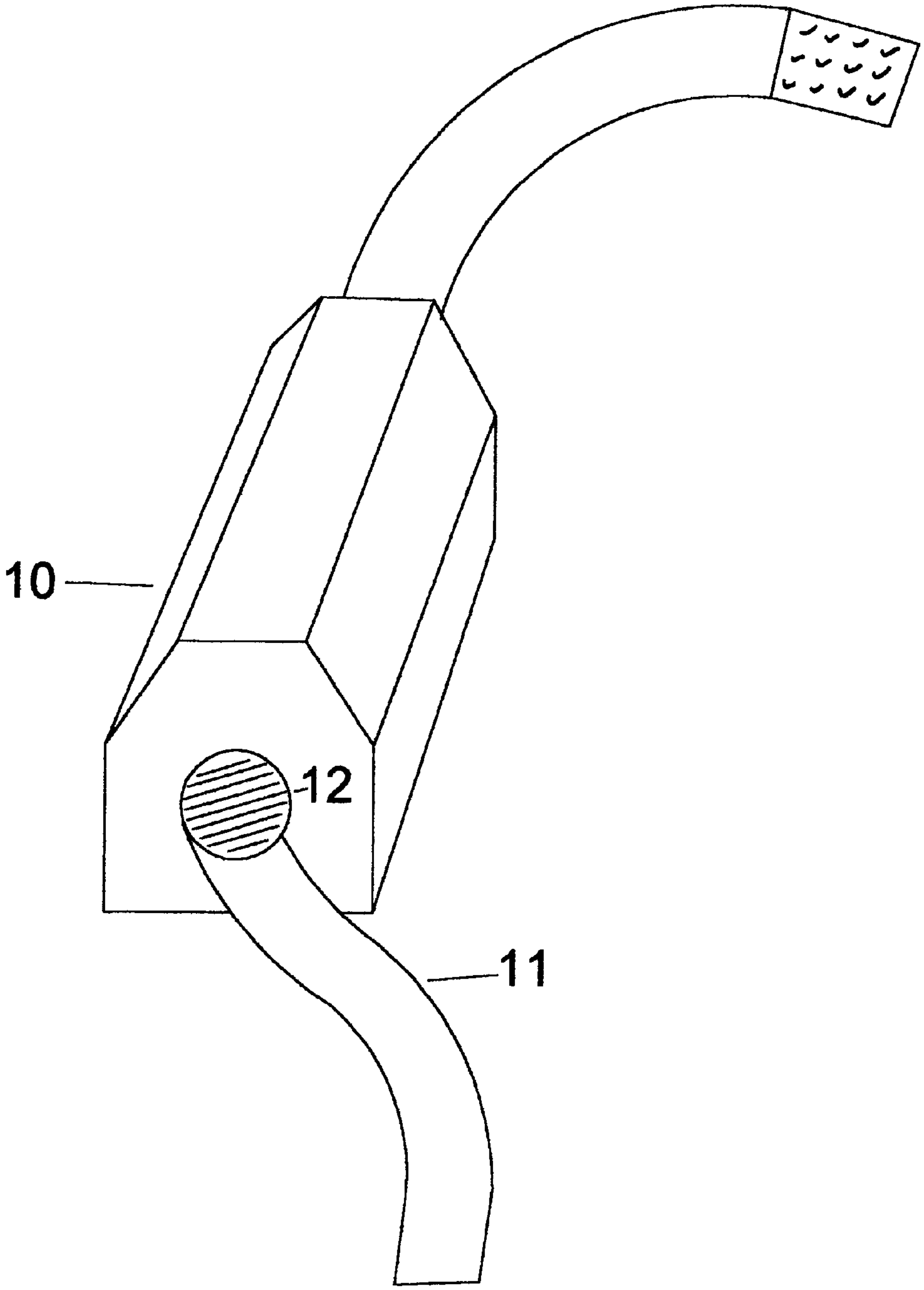
FIG. 3 shows the assembly of the toe support.

A toe support (10) is positioned upon and secured to the foot plate (2) by means of a strap (11) that is secured and tightened to itself by hook and loop (Velcro) on the underside of the foot plate. FIG. 3 demonstrates said toe support. The main body of the toe support (10) is shaped from readily available semi-rigid polystyrene foam (such as that used for a swimmer's "noodle"). A round hole through the center of the main body accommodates a tightly fitting section of a 1 inch diameter wooden dowel (12) that serves to stiffen the structure and secure the strap (11).

Figure 4:
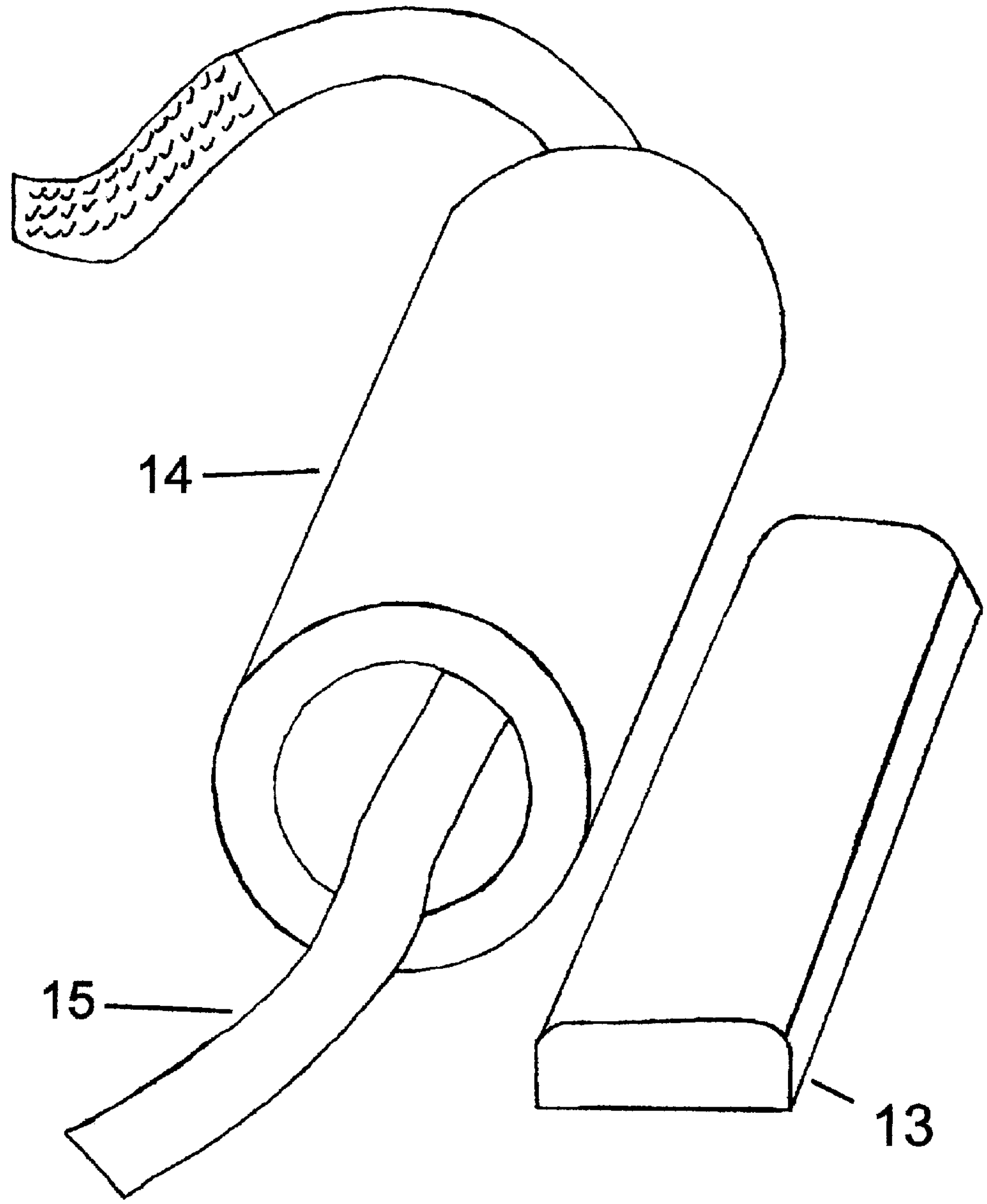
FIG. 4 shows the arch support and arch support insert.

An arch support (14), as shown in FIG. 1, is similarly positioned and secured by a strap (15). FIG. 4 demonstrates said arch support. The arch support (14) is a comprised of a 4 inch length of hollow cylinder foam material, such as some materials that are used to insulate water pipes. The arch support (14) is soft and collapsible but can offer resistance to the arch and presses broadly and gently into the arch. An arch support insert (13), composed of a variable thickness of semi rigid foam can be inserted into the arch support (14) to effect a controllable amount of height.

Figure 2:
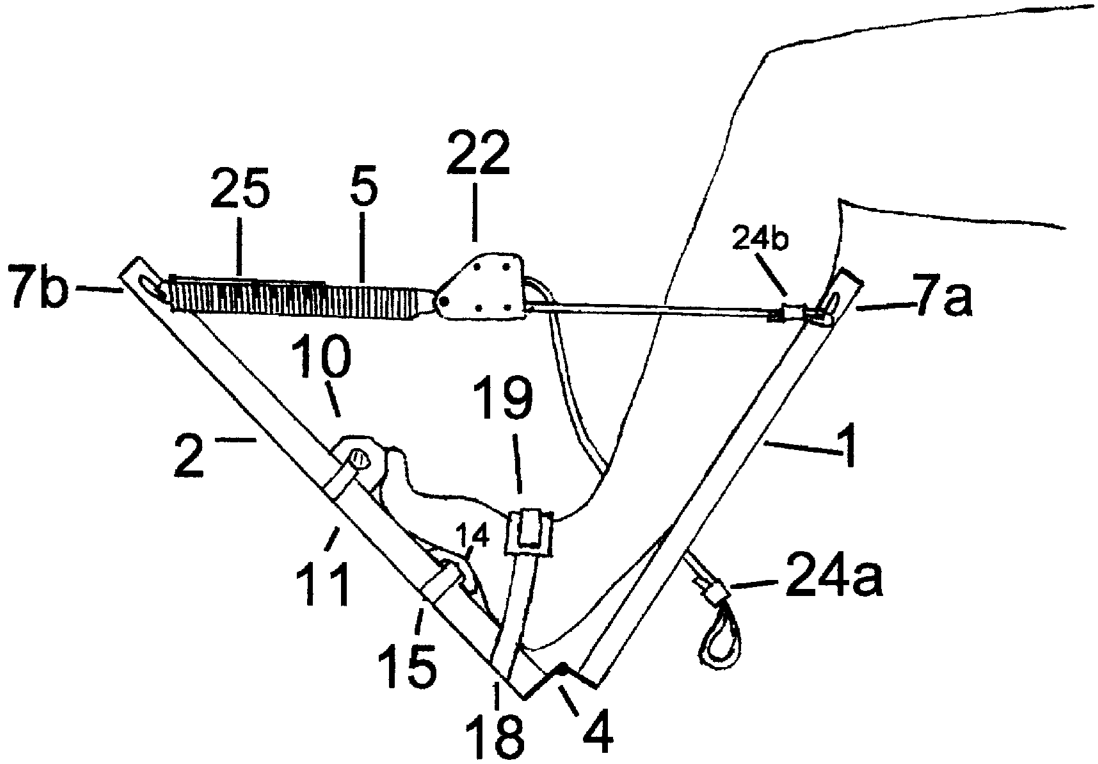
FIG. 2 shows the device applied to the foot and lower leg.
Figure 5:
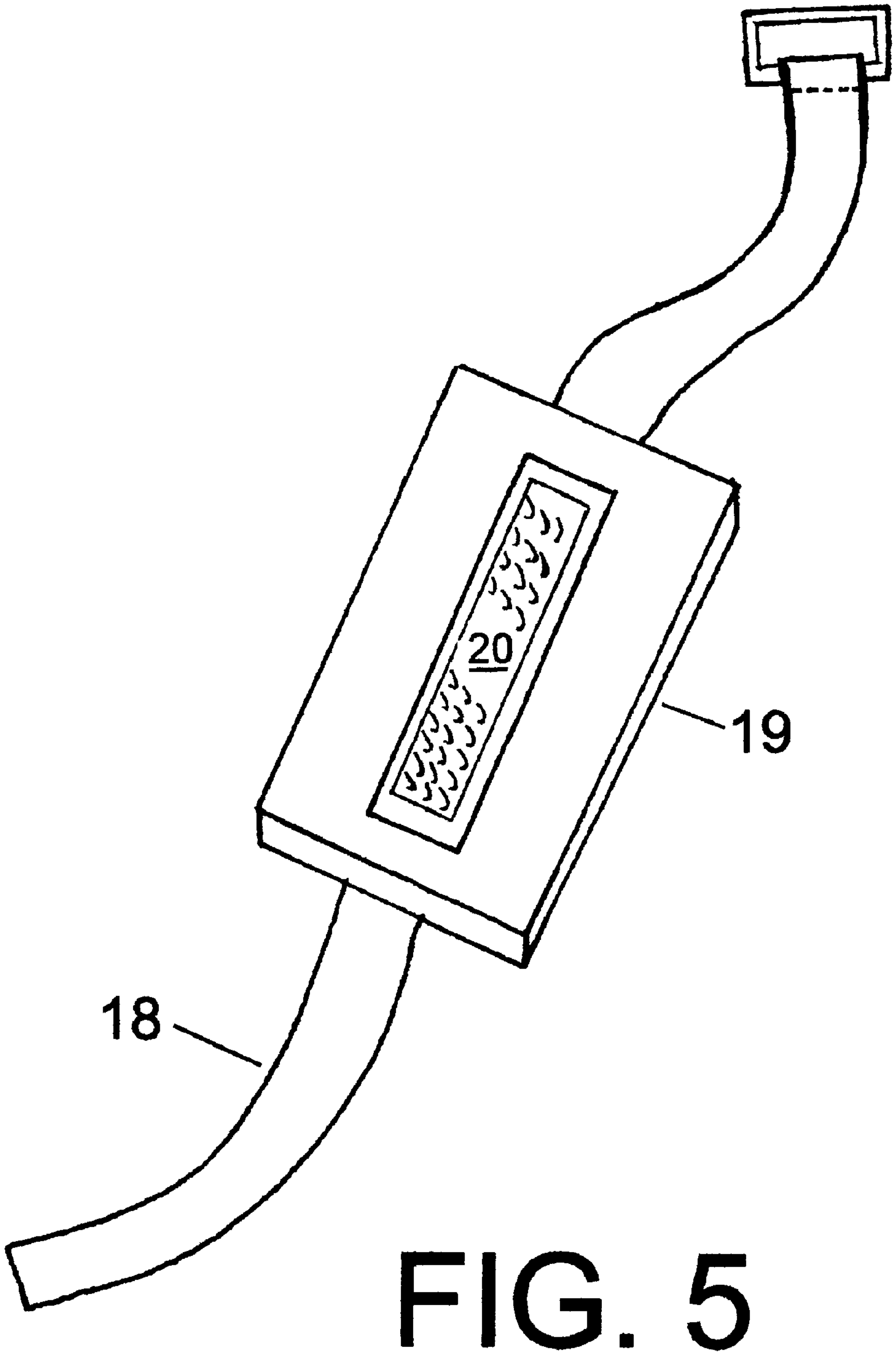
FIG. 5 shows the assembly of the foot strap.

FIG. 2 shows a typical application of the device. The back of the heel has been aligned with the back edge of the heel alignment guide (16) (shown in FIG. 1). The arch support (14) is positioned in the center of the arch and secured by the strap (15) to the foot plate (2). The toe support (10) is positioned to cause significant toe bend and is secured by the strap (11) to the foot plate (2). The foot itself is secured by a foot strap (18). Said foot strap, also evident in FIG. 1, is detailed in FIG. 5. An instep cushion (19) is fashioned from a high-density foam material, reinforced with cloth, and provided with two slots to feed through the foot strap (18). The foot strap (18) is secured to the bottom of the foot plate (2) with staples. With the instep cushion (19) positioned over the instep, the foot strap (18) is fed through its belt loop, pulled back tightly over the instep and secured by a Velcro connector (20), shown in FIG. 5.

Tensioning is achieved by pulling the loose rope end, associated with ferrule (24A), of the cinching device (22). Tension is released by pressing the release lever of the cinching device (22) (previously noted as rope ratchet (U.S. Pat. No. 5,368,281)), while simultaneously pulling back and then releasing the loose rope end through the ratchet mechanism.

Figure 6:
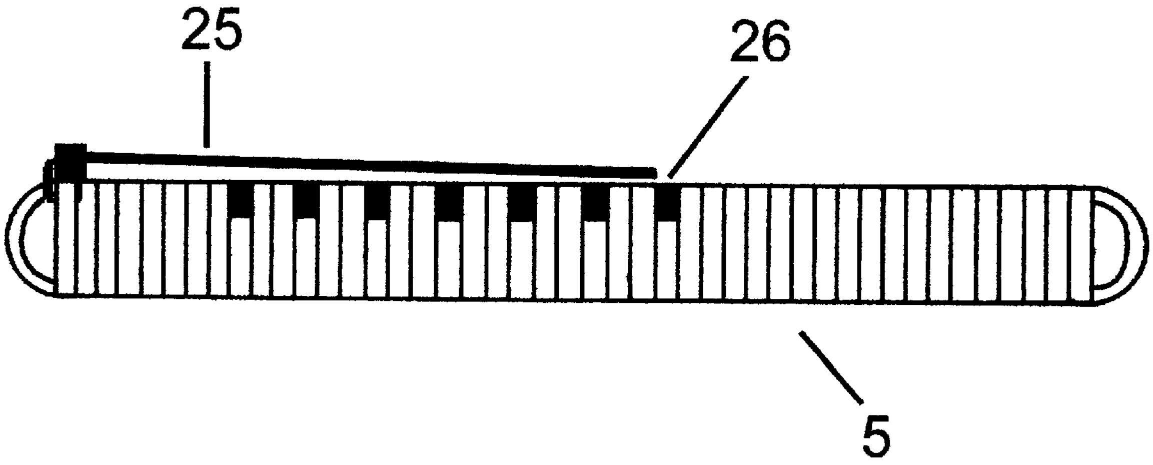
FIG. 6 shows the tensioning spring with tension level markings and tensioning gauge.

FIG. 6 details the assembly of the spring (5) as a tension measurement system. A gauge stick (25) is comprised of a nylon tie cut to length, secured around the first ring of the spring (5) and cemented in place. As the spring (5) is expanded in tension, the end of the gauge stick will align with tension level markings (26) that correspond to discrete tension settings. The length of gauge stick (25) and the position of the tension level markings (26) will vary with the properties of the spring (5) selected for use.

Figure 7:
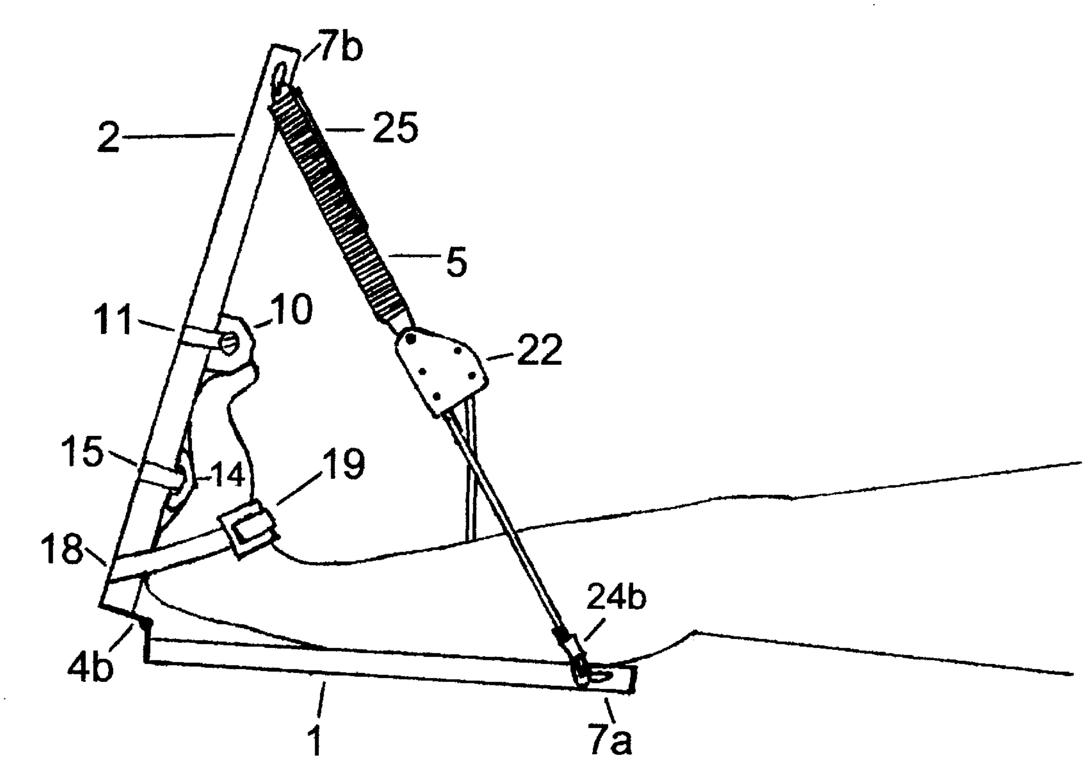
FIG. 7 shows the device being applied to the straightened leg to develop a gastrocnemius stretch.

FIG. 7 shows an alternate application of the device. Simply by straightening the leg at the knee and suspending the device in a horizontal plane, a measure of the stretch is transferred to the gastrocnemius muscle.

Figure 8:
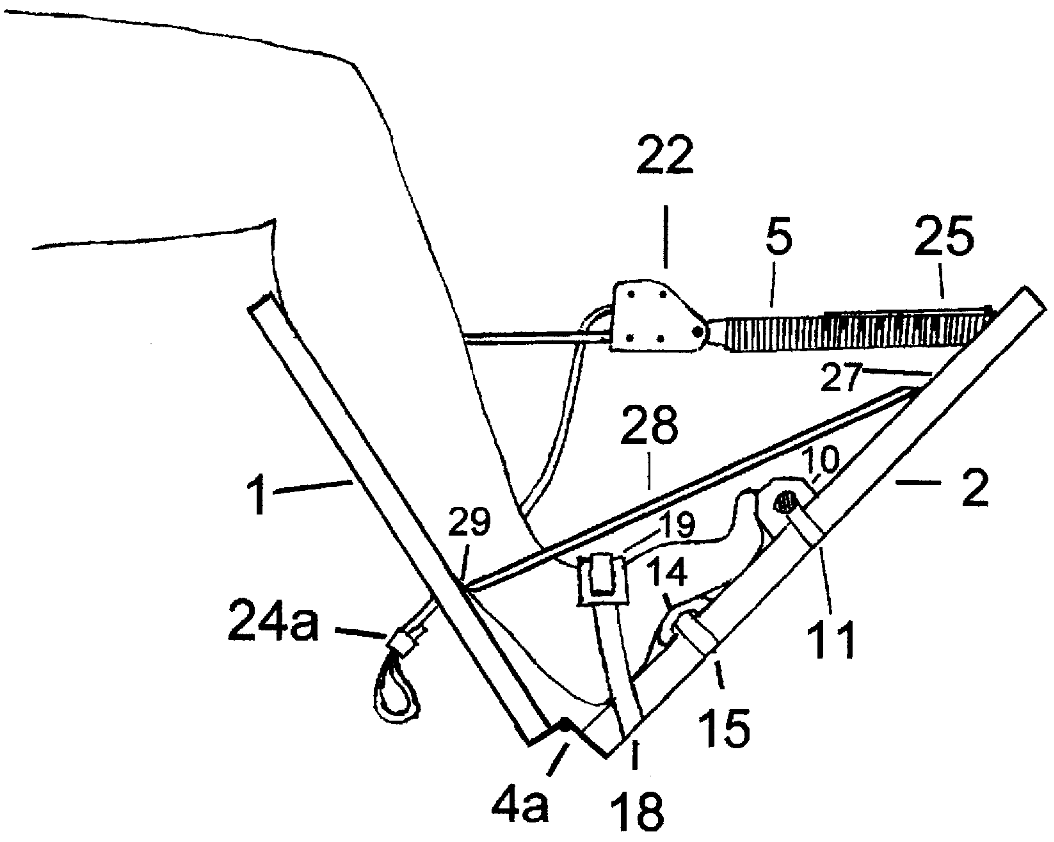
FIG. 8 shows the applied device with the measuring rod in position.
Figures 9A, 9B:
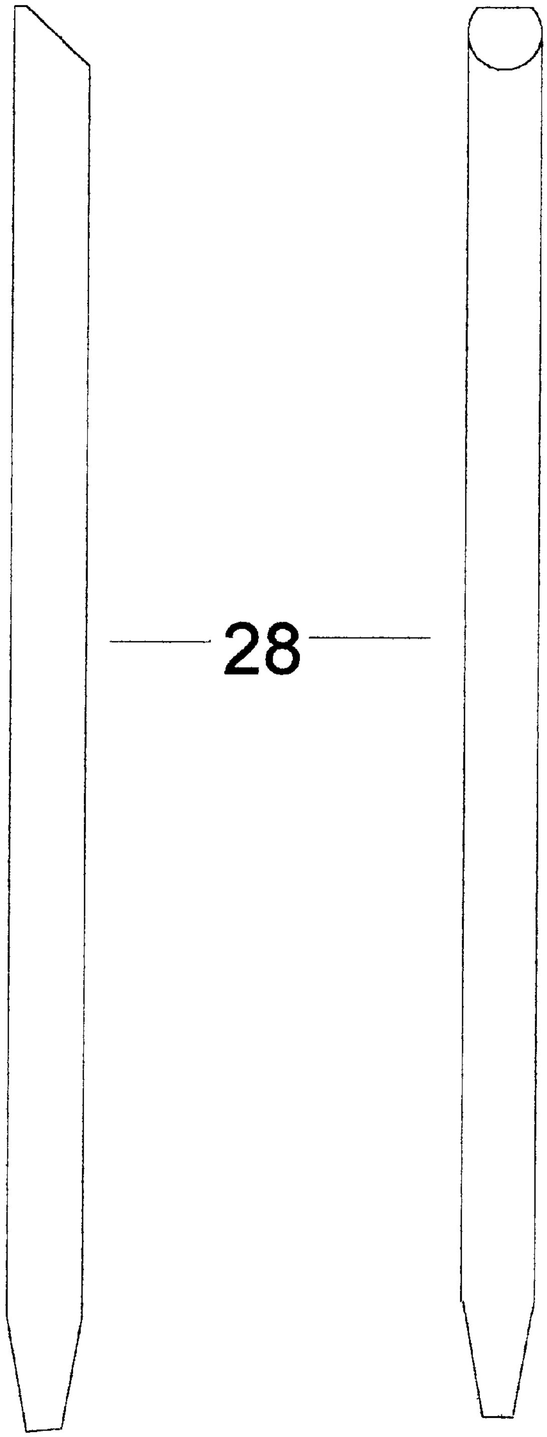
FIG. 9A and FIG. 9B detail the shape of the measuring rod.
Figure 10:
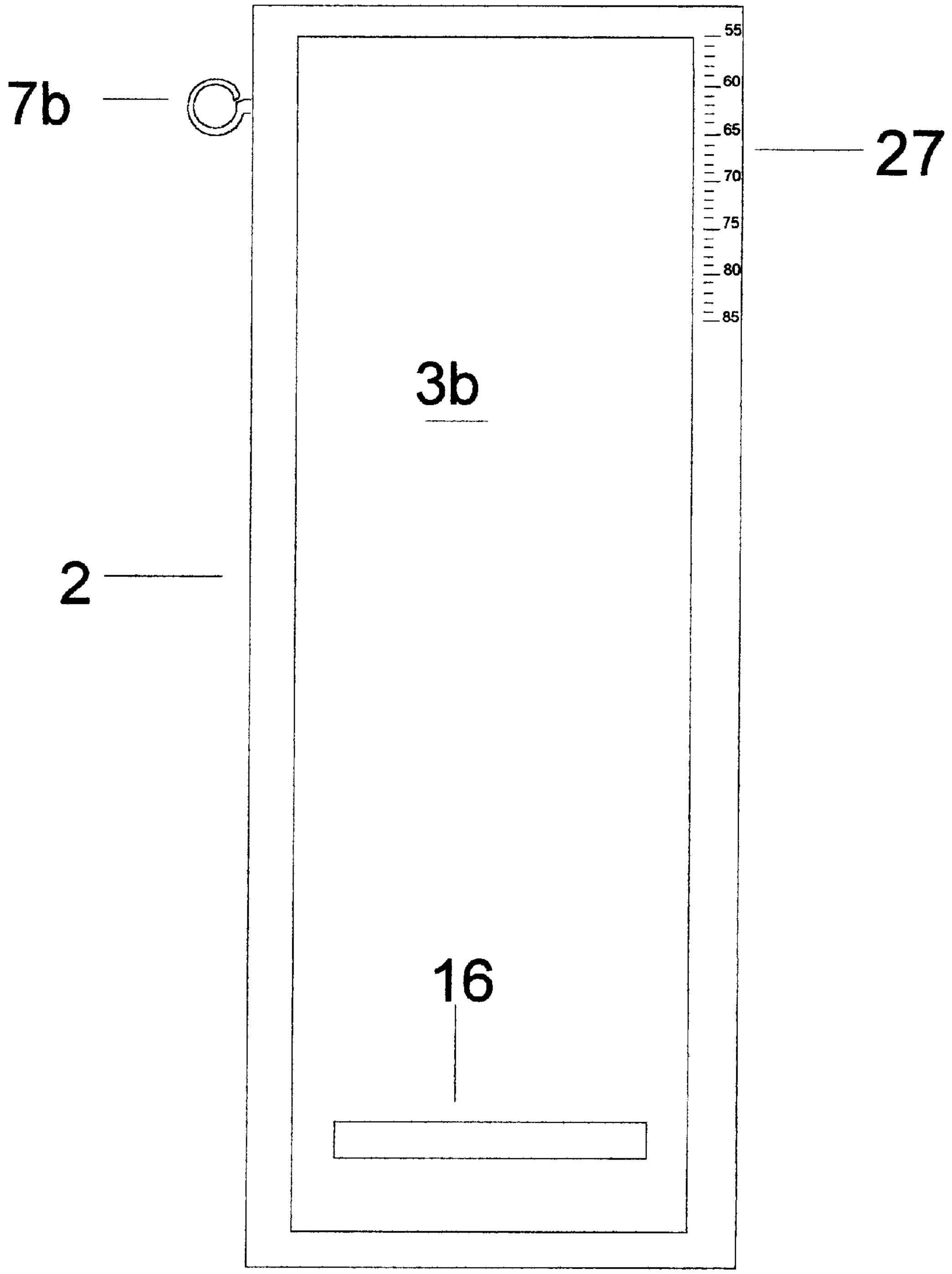
FIG. 10 shows the isolated foot plate with a view of the angle scale.

A means of measuring the angular displacement of the device under a defined amount of tension serves multiple functions. Such a means allows the therapist to evaluate the initial flexibility of the Achilles tendon-plantar fascia system as well as the improvement of flexibility over time. A convenient and ready means of this measurement would also lend to an evaluation of the relative effectiveness of various protocols. Knowing and understanding this information would likewise be an aide to the user in their rehabilitative efforts. In addition, such measurements can serve to verify the effectiveness of the toe support (10) and the arch support (14) in transferring the stretch to the plantar fascia, as angular displacement at a constant tension will vary with the addition of the arch support (14) and toe support (10). This process can be simply achieved by the use of a measuring rod (28), the use of which in is demonstrated in FIG. 8. The construction of the measuring rod (28) is shown in profile in FIG. 9A and in a top view in FIG. 9B. Said measuring a rod is fashioned from a 15 inch length of wooden dowel, 5/16 inch in diameter in the preferred embodiment but could be fashioned from other materials and in other dimensions. The bottom, or conical, end of the measuring rod (28) is inserted into a locating hole (29) which is visible on the leg plate (1) of FIG. 1. The locating hole (29) is a shallow depression barely larger in diameter than the flattened conical end of the measuring rod (28). The top, or beveled, end of said measuring rod is shown to have a flattened edge that will align with a position on a scale (27), shown in FIG. 10, imprinted on the foot plate (2) and corresponding to the angular displacement of the two plates.

While this presentation describes in some specificity the construction and use of this device, it is not intended to limit sensible or obvious variation in its construction and use. The scope of this invention should be determined by the appended claims.

I claim:

1. A therapeutic leg and foot device for passively and developmentally stretching the plantar fascia and soleus and gastrocnemius muscles of the lower leg, the device comprising:

a) a leg plate sized and configured to be against the calf of the user and establishing a plane of resistance against the calf;

b) a foot plate sized and configured to be against the length of the bottom of the user's foot, establishing a plane of resistance against the bottom of the foot and adapted to extend beyond the foot to gain mechanical advantage to leverage the ankle joint, said foot plate being open on top and having a removable toe support;

c) a hinge connecting said leg plate to said foot plate, the hinge solely rotating about a single axis and d) a dynamic tensioning mechanism attaching said leg plate to a portion of said foot plate and tension loading said foot plate and said leg plate against the foot and the calf when in use, resulting in a leveraged force applied against the plantar surface of the forefoot and not causing any fixation of the angle between said leg plate and said foot plate, said dynamic tensioning mechanism comprised of:

i) an elastic tensioning element and ii) a means for adjusting and securing tension levels.

2. The device of claim 1 wherein said foot plate includes an adjustable arch support for enhancement of plantar fascia stretch.

3. The device of claim 1 wherein said device includes a strap adapted to secure the foot against said foot plate.

4. The device of claim 1 wherein said foot plate and said leg plate are padded to cushion and stabilize the foot and leg within said device.

5. The device of claim 1 wherein said device further comprises a gauge for displaying tensioning force.

6. The device of claim 1 wherein said foot plate has a heel placement guide to assure proper and consistent placement of the foot within the device.

7. A therapeutic leg and foot device for passively and developmentally stretching the plantar fascia and soleus and gastrocnemius muscles of the lower leg, the device comprising:

a) a leg plate sized and configured to be against the calf of the user and establishing a plane of resistance against the calf;

b) a foot plate sized and configured to be against the length of the bottom of the user's foot, establishing a plane of resistance against the bottom of the foot and adapted to extend beyond the foot to gain mechanical advantage to leverage the ankle joint;

c) a hinge connecting said leg plate to said foot plate, the hinge solely rotating about a single axis;

d) a dynamic tensioning mechanism attaching said leg plate to a portion of said foot plate and tension loading said foot plate and said leg plate against the foot and the calf when in use, resulting in a leveraged force applied against the plantar surface of the forefoot and not causing any fixation of the angle between said leg plate and said foot plate, said dynamic tensioning mechanism comprised of:

i) an elastic tensioning element and ii) a means for adjusting and securing tension levels;

(e) a gauge that displays tension force relative to the expansion of said tensioning element; and f) a means for measuring the angular displacement between said leg plate and said foot plate, the means for measuring comprising:

i) a triangulating measuring rod;

ii) a calibrated scale, whereby the triangulating rod and calibrated scale reveal an angle of dorsiflexion and iii) a heel placement guide to assure proper and consistent placement of the foot within the device.

8. The device of claim 7 wherein said foot plate includes an adjustable toe support for enhancement of plantar fascia stretch.

9. The device of claim 7 wherein said foot plate includes an adjustable arch support for enhancement of plantar fascia stretch.

10. The device of claim 7 wherein said device includes a strap adapted to secure the foot against said foot plate.

11. The device of claim 7 wherein said foot plate and said leg plate are padded to cushion and stabilize the foot and leg within the device.

12. A therapeutic leg and foot device for passively and developmentally stretching the plantar fascia and soleus and gastrocnemius muscles of the lower leg, the device comprising:

a) a leg plate sized and configured to be against the calf of the user and establishing a plane of resistance against the calf;

b) a foot plate sized and configured to be against the length of the bottom of the user's foot, establishing a plane of resistance against the bottom of the foot and adapted to extend beyond the foot to gain mechanical advantage to leverage the ankle joint, said foot plate being open on top and having a removable toe support;

c) a hinge connecting said leg plate to said foot plate, the hinge solely rotating about a single axis;

d) a dynamic tensioning mechanism attaching said leg plate to a portion of said foot plate and tension loading said foot plate and said leg plate against the foot and the calf when in use, resulting in a leveraged force applied against the plantar surface of the forefoot and not causing any fixation of the angle between said leg plate and said foot plate, said dynamic tensioning mechanism comprised of:

i) an elastic tensioning element and ii) a means for adjusting and securing tension levels; and (e) a gauge that displays tension force relative to the expansion of said tensioning element.

13. The device of claim 12, wherein said foot plate includes a removable toe support for enhancement of plantar fascia stretch.

14. The device of claim 12, wherein said foot plate includes an adjustable arch support for enhancement of plantar fascia stretch.

15. The device of claim 12, wherein said device includes a strap adapted to secure the foot against said foot plate.

16. The device of claim 12, wherein said foot plate and said leg plate are padded to cushion and stabilize the foot and leg within said device.

17. The device of claim 12, wherein said foot plate has a heel placement guide to assure proper and consistent placement of the foot within the device.

* * * * *